United States Patent [19]

Cappa et al.

[11] Patent Number: 4,592,384
[45] Date of Patent: Jun. 3, 1986

[54] COMMUTATOR FEEDING DEVICE FOR A DEMAND VALVE INTENDED FOR INTRODUCING BREATHABLE AIR INTO A COMPRESSED AIR BREATHING APPARATUS

[75] Inventors: Giulio Cappa, Milan; Romano Moscatelli, Rome, both of Italy

[73] Assignee: Sekur S.p.A., Milan, Italy

[21] Appl. No.: 611,888

[22] Filed: May 18, 1984

[30] Foreign Application Priority Data

May 19, 1983 [IT] Italy .................................. 21177 A/83

[51] Int. Cl.⁴ .............................................. A61M 16/00
[52] U.S. Cl. ................................. 137/494; 128/204.26; 128/205.24; 137/908
[58] Field of Search ...................... 128/204.26, 205.24; 137/494, DIG. 9

[56] References Cited

U.S. PATENT DOCUMENTS 2,552,595  5/1951  Seeler .............................. 128/204.26
4,207,884  6/1980  Isaacson ...................... 128/204.26 X

FOREIGN PATENT DOCUMENTS 152622  2/1938  Austria ............................. 128/205.24

Primary Examiner—Robert G. Nilson
Attorney, Agent, or Firm—Stevens, Davis, Miller & Mosher

[57] ABSTRACT

A commutator feeding device for a demand valve, comprising a transducer adapted for controlling the movement of a shutter element for feeding predetermined quantities of air into a chamber of said demand valve in response to a pressure variation taking place inside said chamber, said transducer being activated following the shifting of a deformable membrane. The device comprises a spring, disposed inside a small piston, adapted for resting on said membrane, said small piston being provided with radial stakes or spokes, each one of which is adapted to rest on the active surface of a corresponding helicoidal profile cam, with manually operable actuating means being predisposed for controlling the rotation of said small piston around its own axis, and hence the axial shifting of the small piston itself in the spring-compressing sense.

9 Claims, 11 Drawing Figures

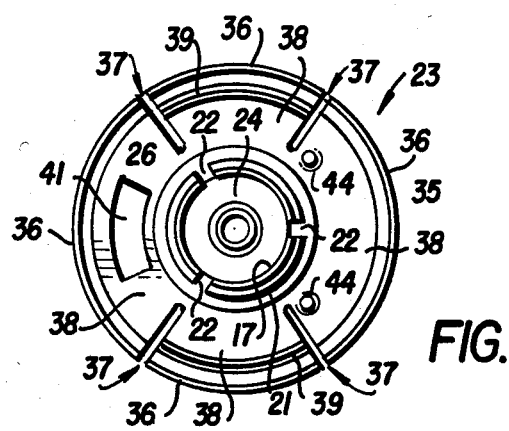
FIG. 6
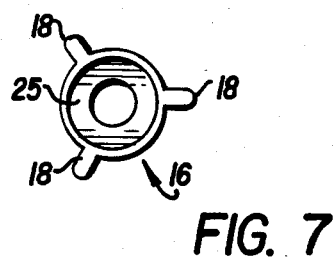
FIG. 7
FIG. 8
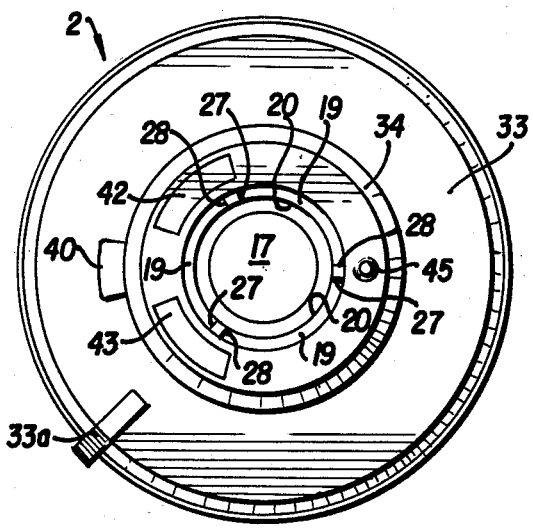
FIG. 10
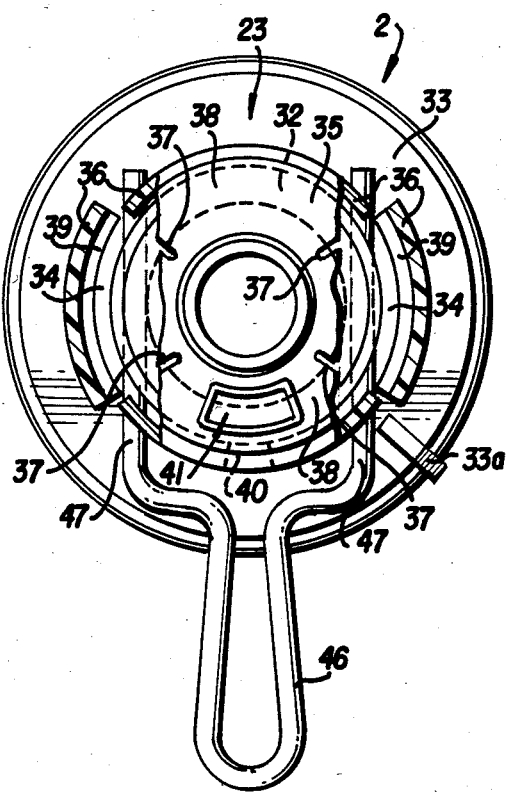
FIG. 9

COMMUTATOR FEEDING DEVICE FOR A DEMAND VALVE INTENDED FOR INTRODUCING BREATHABLE AIR INTO A COMPRESSED AIR BREATHING APPARATUS

DESCRIPTION

The present invention relates to a commutator feeding device for a demand valve intended for introducing breathable air into a compressed air breathing apparatus; in particular, inside the mask of the compressed air breathing apparatus itself.

The demand valve, along with which the commutator device of the invention may be utilized, is of the type that comprises a transducer adapted for controlling the movement of a shutter element for feeding predetermined quantities of air into a chamber of the demand valve itself, following a pressure variation that occurs in said chamber. The above-said transducer comprises, substantially, a deformable membrane upon one wall of which there rests a stylus that is made fast with a rod connected to the previously mentioned shutter element in such a way that, following a deformation of the membrane, the position of said shutter element is varied. One wall of said membrane also constitutes one of the walls that delimit the above-said chamber, and hence on one of its surfaces the pressure that exists inside the chamber itself acts, while on the other surface of the same wall atmospheric pressure is caused to act.

The demand valves of the type described are adapted for being utilized substantially in two different configurations. In a first of these configurations, the above-mentioned transducer is predisposed for controllling the opening of the shutter element for the purpose of feeding air into the above-said chamber only when the pressure inside it is lower than atmospheric pressure. For predisposing the demand valve for functioning as in said first configuration, it is necessary that on a first surface of the previously mentioned membrane wall (that also constitutes one of the surfaces which delimit the said chamber), the pressure existing inside the chamber itself acts, while atmospheric pressure acts on a second surface of the same wall. In this way, said wall is brought into equilibrium between the two pressures, and hence it is able to shift whenever the pressure inside the chamber falls to below atmospheric pressure.

For predisposing the demand valve for functioning as in the second configuration, it is necessary that on said first surface there is also caused to act a predetermined force generated by a spring. Under these conditions, the membrane may shift for controlling the opening of the shutter element only when the pressure inside the chamber is higher than atmospheric pressure and when it can overcome the elastic reaction applied to the spring itself.

On the basis of the present invention, a commutator device for a demand valve is provided of the type described, which structurally is very simple and which may be set up and dismantled with considerable facility, and whose functioning is safe and reliable.

On the basis of the present invention, a commutator device for a demand valve intended for introducing breathable air into a compressed air breathing apparatus is provided and, in particular, inside the mask of said compressed air breathing apparatus, with said demand valve comprising a transducer adapted for controlling the movement of a shutter element for feeding predetermined quantities of air into a chamber of said demand valve in response to a pressure variation taking place inside the latter, with said transducer being actuated following the shifting by a deformable membrane adapted for measuring the pressure that exists in said chamber, with said device being adapted for switching over said distributor from a first configuration, wherein on a first surface of said membrane the pressure which exists inside said chamber acts, and wherein on a second surface of the membrane itself atmospheric pressure acts, into a second configuration, wherein on said second surface there is also caused to act a predetermined force generated by a spring, characterized in that said spring is disposed inside a small piston adapted to rest on said second surface of said membrane and axially mobile inside a cylindrical hole made in a casing cover of said demand valve, said small piston being provided with radial stakes, each one of which is adapted to rest upon the active surface of a corresponding helicoidal profile cam made on the lateral surface of said cylindrical hole, and with manually operable actuating means being arranged for controlling the rotation of said small piston around its own axis, and hence, the axial shifting of the small piston itself in the spring compressing sense, for taking said demand valve from said second configuration to said first configuration.

On the basis of this invention, the above-said actuating means comprise a revolving sleeve, coaxial with said small piston and interposed between the latter and said cylindrical hole, said sleeve being provided with axial slits, in each of which is inserted one of said stakes, and provided with an actuating handle that protrudes above the said cover.

For a still better understanding of the invention, there now is given, by way of example, a description of one of its particular embodiments, with reference to the accompanying drawings wherein:

FIG. 6 shows a plan view, seen from below, of a sleeve that forms part of the device of this invention;

FIG. 7 shows a plan view of a small piston that forms part of this device;

Figure 11:
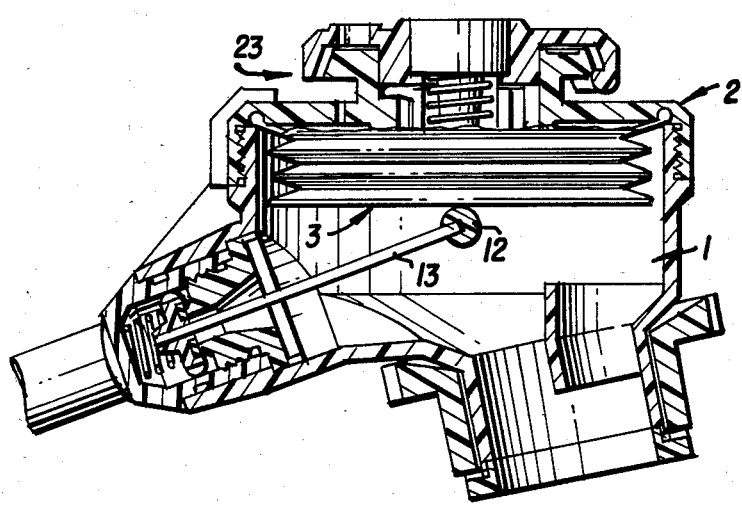

FIG. 8. shows a plan view, seen from above, of a cover of the demand valve in which the device is incorporated;

FIGS. 9 and 10 show two partial sections of the device adapted for pointing out in detail the means for dismantling the device itself, and FIG. 11 illustrates a demand valve which uses the commutator of the invention.

Figure 1:
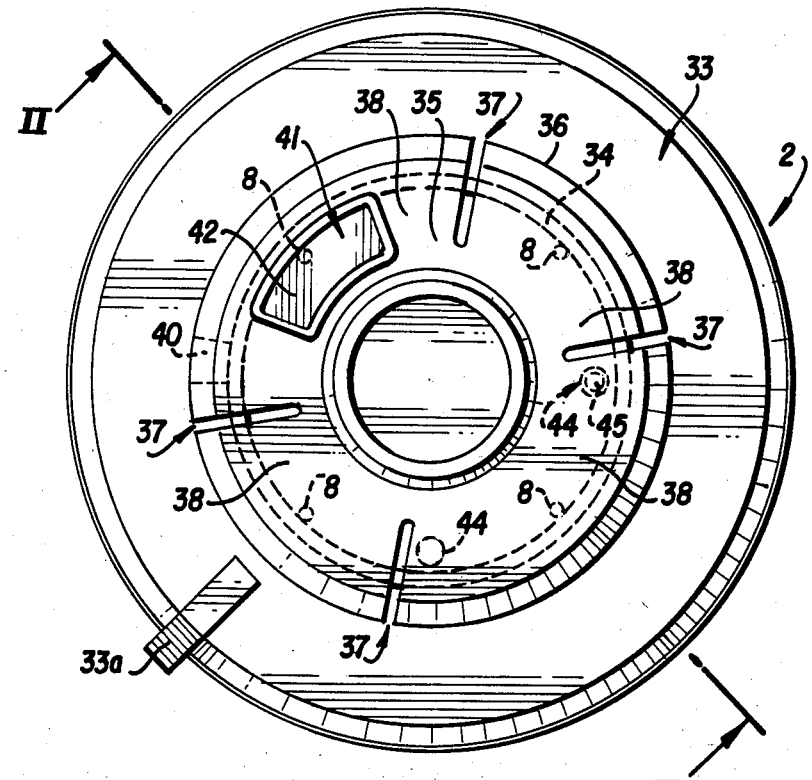
FIG. 1 shows a plan view of the demand valve in which the commutator device of the present invention is incorporated.
Figure 2:
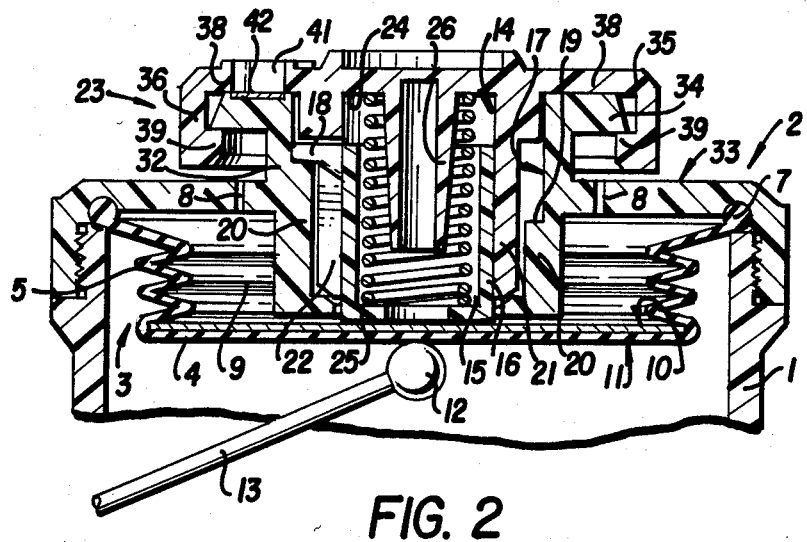
FIG. 2 shows a cross-section of the demand valve of FIG. 1 through plane II—II of FIG. 1.

First, with reference to FIGS. 1 and 2, the commutator device of the invention is destined for a demand valve of the type that can be seen partially in FIGS. 1 and 2, as fully illustrated in FIG. 11, and which comprises a casing 1 and a cover 2, connectable in any convenient way to the casing itself, for defining inside them a substantially cylindrical chamber 3. The demand valve comprises, moreover, a deformable membrane provided with a substantially flat wall 4 and a lateral substantially cylindrical wall 5 that is provided with a series of corrugations for rendering it axially deformable in bellows-like fashion. The upper circular edge 7 of said membrane is blocked or tightly secured between the cover 2 and the casing 1, in the manner shown in FIG. 2. It should be noted that the transducer shown in FIG. 11 is merely one example of a transducer which can be used in accordance with the present invention.

A series of holes 8 in the cover 2 place the atmosphere into communication with an internal cavity 9 defined within the deformable membrane itself. In this way, the atmospheric pressure acts on the surface 10 of the wall 4 of the membrane, while the pressure existing inside the chamber 3 acts on the other surface 11 of the wall 4.

A transducer is adapted to control the opening of the shutter element (not shown) for feeding air into the chamber 3. The air is furnished by a source of compressed air. Said transduce comprises a stylus 12 adapted to rest on the surface 11 of the membrane wall 4, and an actuating rod 13 connected with the above-said shutter element in such a way that, following the axial shifting of the wall 4, the actuating rod 13 is caused to rotate for varying the passage hole for air controlled by the shutter element.

The described demand valve is predisposed for functioning in two different configurations. In the first of these, on the surfaces 10 and 11 of the membrane wall 4, there only act, respectively, the atmospheric pressure and the pressure which exists inside the chamber 3. Hence, in this configuration, with the membrane wall 4 being equilibrated between the above-said two pressures, the opening of the shutter element is controlled for allowing the entry of air into the chamber 3 itself when the pressure inside it is below atmospheric pressure (negative pressure). The demand valve, moreover, is in a condition for functioning in a second configuration, wherein on the surface 10 of the membrane wall 4 there is also caused to act the force exerted by a spiral spring 15, which is interposed (in a manner to be explained further on in the text) between the cover 2 and the deformable membrane itself. The said spring 15 exerts said axial force on the membrane wall 4 through a small piston 16 that is axially mobile with respect to the cover 2.

Therefore, in said second operative configuration, since on the membrane wall 4 there act, apart from the pressures existing in the chambers 9 and 3, also the forces exerted by the spring 15, the opening of the shutter element being controlled whenever the pressure inside the chamber 3, although still remaining higher than atmosphere pressure (positive pressure), falls to below a predetermined value (equal to the elastic reaction of the spring divided by the surface area 11 of the membrane).

On the basis of this invention, then, the small piston 16 is provided with a plurality of radial stakes or projections, each one of which is adapted to lean or bear on the active surface 19 (FIG. 5) of a corresponding cam 20, which presents a substantially helicoidal profile and the internal surface of which is provided with a hole 17 in the cover 2. The device comprises, moreover, a rotatable sleeve 21 which is interposed between said surface and the small piston 16. Said sleeve 21 is provided with a plurality of axial slits 22 (FIG. 5) in each of which there is slidingly inserted one of the stakes or projections 18 (as can be seen clearly in FIG. 2). The said sleeve 21 is, moreover, provided with an actuating handle 23 made all in one piece with the sleeve 21 itself, and adapted for controlling the rotation of said sleeve 21.

An annular surface 24 (FIG. 2) inside the sleeve 21 constitutes a resting or bearing surface for the spring 15, which is interposed between said surface 24 and another resting or bearing surface 25 made inside the small piston 16. An appendix or extension 26 of the handle 23 protrudes axially inside the sleeve 21 and is inserted into the spring itself.

In the form described, inside the hole 17 there are provided three cams 20 having a phase displacement angle of substantially 120°, with each of them (as can clearly be seen in FIG. 5) comprising a substantially helicoidal active surface 19 that is coaxial with the axis of the hole 17 and prearranged for constituting a supporting surface for a corresponding stake 18 of the small piston 16, and a corresponding pair of substantially axial stopping surfaces 27 and 28, disposed laterally with respect to said active surface 19 and adapted for delimiting the rotation of the small piston 16 itself with respect to the cover, in a way that shall be explained further on in the text.

The cover 2 comprises, moreover, an annular relief 32 that protrudes axially above the surface 33 of the cover itself, and which is provided with a substantially annular rim 34. The handle 23 presents a first wall 35 that is substantially flat and circular and adapted for superimposing the annular relief 32 having an annular rim 34, as well as a second cylindrical wall 36 that is disposed in the outermost peripheral position with respect to the annular rim 34 (FIG. 2).

For convenience, in the first and second walls 35 and 36 of the handle 23, radial grooves 37 are provided that are adapted for defining the sectors of the handle 38 (FIG. 1), and the cylindrical wall 36 of each of these sectors is provided with radial teeth 39 (FIG. 2) adapted for co-operating with the annular rim 34 in such a way as to allow a spring fitting of the handle 38 to the cover 2.

From the annular relief 32 there protrudes radially a pad 40 adapted to come into contact with stopping teeth 39 of the sector 38, for limiting the end-of-rotation of the handle 23 with respect to the cover 2 between two predetermined angular positions, which are out of phase with each other, at a suitable angle.

An aperture 41 is made in the wall 35 of the actuating handle 23. Said aperture 41, when said handle 23 is moved to one of the two above-mentioned angular positions, is adapted for uncovering a corresponding surface-of-reference 42 or 43 made on the annular rim 34 (see FIG. 5).

However, for convenience, a radial relief 33a is made on the cover 2 above the upper surface 33 of the cover itself. This relief 33a is aligned with the surface-of-reference 43, as can clearly be seen in FIG. 3.

On the lower surface of the wall 35 of the cover 23, moreover, a pair of cavities 44 is provided (see FIG. 5), each one of which is adapted to co-operate with a corresponding protuberance 45 made on the rim 34 in such a way as to act as a spring stop whenever one of the two above-mentioned angular positions is reached.

The functioning of the commutator device of this invention takes place in the following manner.

Figure 5:
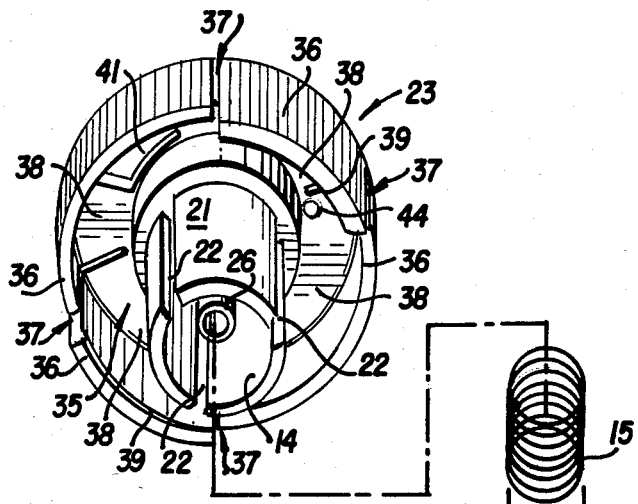
FIG. 5 shows an exploded perspective view adapted to illustrate the main elements of the device of the present invention.
Figure 5:
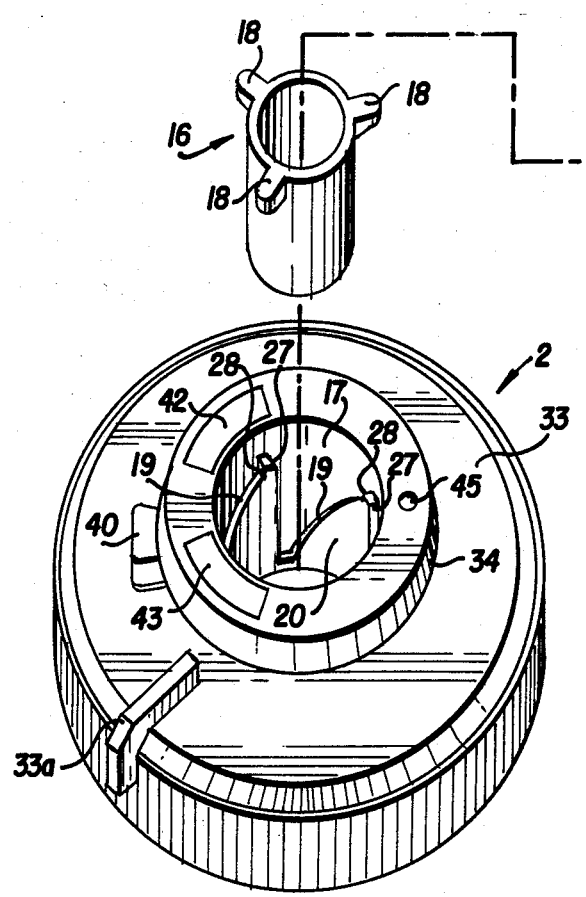

Let us suppose that the commutator device has been set up in such a way as to be disposed in the previously defined first configuration, i.e., on whose surface 10 and 11 of the membrane wall 4 there act only atmospheric pressure and the pressure existing inside the chamber 3. In this configuration, the handle 23 (FIG. 1) has been completely rotated in the clockwise direction (shown in FIG. 1) until the teeth 39 of one of the sectors 38 stops against the pad 40 (FIG. 5). In the same configuration, the aperture 41 uncovers the surface-of-reference 42 (FIG. 1) in such a way as to furnish a visual indentification of the configuration wherein the commutator device is found.

When the handle 23 has been rotated in the above-indicated manner, the slits 22 of the sleeve 21 are found in an angular position with respect to the cover 2 in such a way as to carry the stakes 18 of the small piston 16 so as to be disposed substantially on the initial, more raised, part of the active surface 19 (FIGS. 2 and 5) of the cam 20 (as has been shown in FIG. 2). In this configuration, the small piston 16 is positioned completely inside the hole 14 of the sleeve 21 (as can be clearly seen in FIG. 2) and hence, it does not exert any action upon the surface 10 of the membrane wall 4. In said configuration, each stake 18 is stopped by the corresponding blocking surface 28 (FIG. 5) that delimits, from one side, each active surface 19 of the cam 20.

Figure 3:
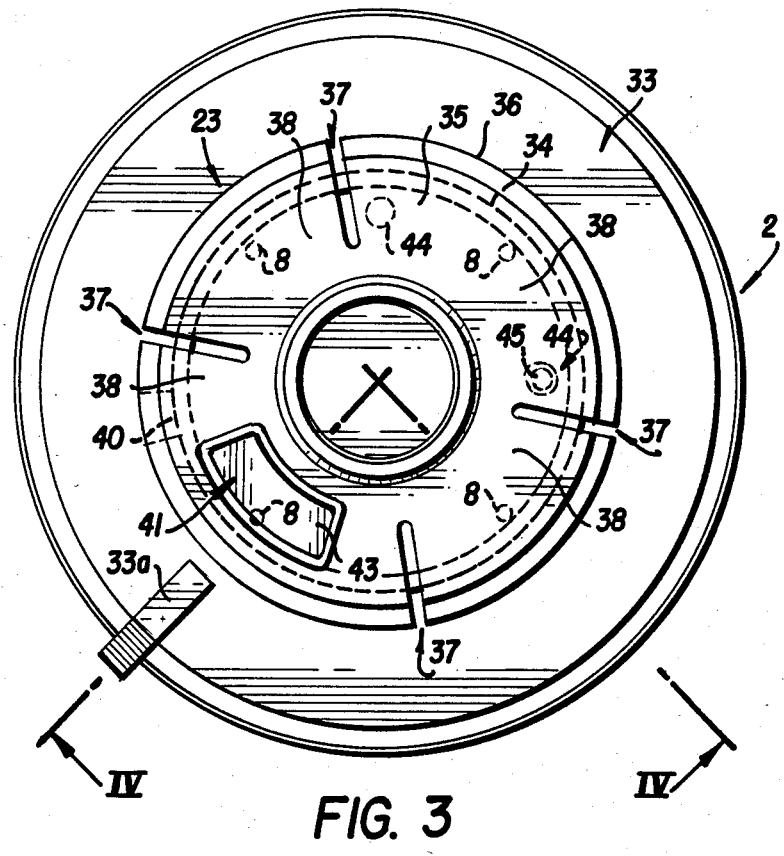
FIG. 3 shows a plan view of the demand valve of FIG. 1 in a different operating position.

When the commutator device is taken or converted to the second configuration wherein, on the surface 10 of the membrane wall 4 there is also made to act the force exerted by the spring 15, the handle 23 becomes rotated in the counter-clockwise direction (FIG. 1) for moving it to the configuration shown in FIG. 3, in which the teeth 39 of one of the sectors 38 stops against the pad 40 (FIG. 5). In this same second configuration, the aperture 41 uncovers the surface-of-reference 43 that is adapted to furnish a visual indication of the new configuration assumed by the device.

In that same second configuration, the aperture 41 is aligned radially with the relief 33a, and hence, in association with the relief itself, is adpated to furnish a tactile indication of the particular configuration wherein the device is set up.

Figure 4:
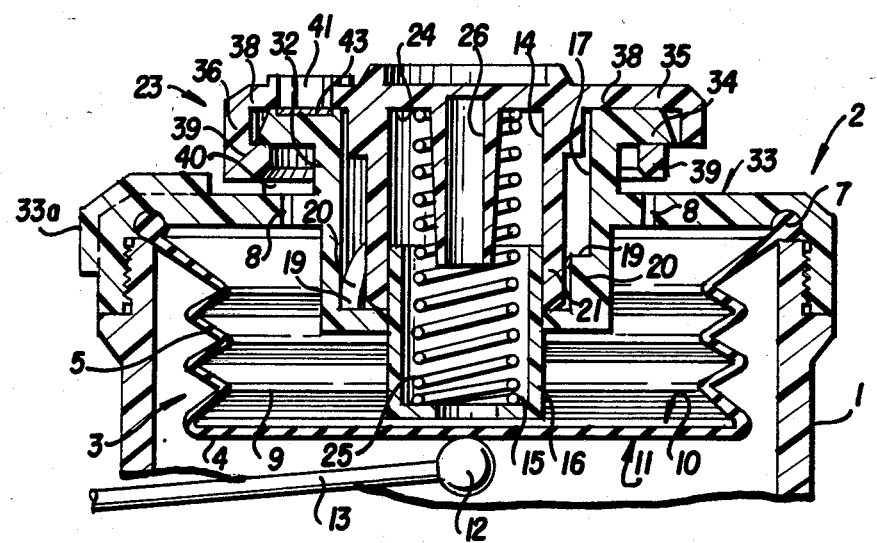
FIG. 4 shows a cross-section of the demand valve of FIG. 3 through plane IV—IV of FIG. 3.

Following the rotation of the handle 23, the sleeve 21 causes the stakes 18 of the small piston 16 to rotate. Said piston 16 under the thrust of spring 15 moves into the hole 14, while the stakes 18 are guided by the active surface 9 of the cam 20. At the end of the above-said rotation, the small piston 16 may rest on the surface 10 of the membrane wall 4, as is shown in FIG. 4, in such a way as to exert upon it the force generated by the spring 15. It is evident that, owing to their conformation, the cams 20 bring about a substantially helicoidal bond of the unilateral type, and the small piston 16 may thereupon assume any relative axial position whatsoever with respect to the hole 14, depending upon the position of the membrane wall 4.

When the device has once again to be commutated into the first configuration, the handle 23 is rotated in the counter-clockwise sense (FIG. 3), and thereupon the sleeve 21 (owing to the coupling of the slits 22 with the stakes 18 of the small piston 16) causes these stakes 18 to rotate, while forcing them to follow the profile of the cams 20 and, as a result of said rotation and owing to the effect of the coupling with the active surface 18 of the cams 20, again taking the small piston 16 into the initial position shown in FIG. 2.

The cavities 44 and the protuberances 45 are positioned in such a way that one of the former become coupled with the latter when the handle 23 is set up or arranged in one of the two configurations shown in FIGS. 1 and 3, in such a way as to create a spring action for achieving the configurations themselves The dismantling of the device described may be done in a very simple way, as shown in FIGS. 9 and 10. For this purpose, it is sufficient to rotate the handle 23 into an intermediate position between those of FIGS. 1 and 3, i.e., in which the aperture 41 is disposed approximately in correspondence with the pad 40, as shown in FIG. 10. By successively introducing a simple implement 46 provided with a pair of substantially parallel arms between the actuating handle 23 and the cover 22, it is easily possible to cause the widening of the lateral walls 36 of the handle itself (as is clearly shown in FIG. 9), in such a way as to release the teeth 39 of the sectors 38 from the corresponding annular rim 34. Under these conditions, by exercising with the implement itself a certain axial force that tends to detach the handle 23 from the cover 2, the former can easily be separated from the latter.

For mounting the device, it is sufficient, after having inserted the spring 15 and the small piston 16 into the hole 14 of the handle 23, to introduce the sleeve 21 into the hole 17 of the cover 2 and to successively exercise a small axial force on the handle 23, in such a way as to elastically deform the lateral walls 36 of the sector 38 for causing the teeth 39 to jump below the annular rim 34.

Hence, the commutator device of the present invention is very simple to mount, and comprises relatively few parts that can be constructed with facility by utilizing thermoplastic materials and the usual technology of pressing and injection molding. Even the mounting of the various parts of the device is rapid and easy. The functioning of this device is, moreover, absolutely reliable and secure.

A specific example of a compressed air breathing apparatus to which the device of this invention may be attached is disclosed in MESA (Mining Enforcement and Safety Administration) of 30 *Code of Federal Regulations* (Mineral Resources, revised as of July 1, 1977). The relevant apparatus can be found in subparts G and H, beginning on pages 19 and 21.

What is claimed is:

1. A commutator device for a demand valve intended for feeding breathable air into a compressed air breathing apparatus, particularly inside the mask of said compressed air breathing apparatus, said demand valve comprising a transducer for controlling the movements of a shutter element for feeding predetermined quantities of air into a chamber of said demand valve, following a pressure variation inside chamber, said transducer being activated by the shifting of a deformable membrane adapted for adjusting to the pressure which exists in said chamber, said device being adapted for commutating said demand valve from (i) one configuration wherein, on a first surface of said membrane, the pressure existing inside said chamber acts and wherein, on a second surface of the membrane itself, the atmospheric pressure acts, and to (ii) a second configuration wherein, on said second surface, a prefixed force generated by a spring is also caused to act, characterized in that said spring is disposed inside of a small piston adapted for resting upon said second surface of said membrane and by being axially mobile inside a cylindrical hole made in a cover of the casing of said demand valve, said small piston being provided with radial stakes, each one of which is adapted to rest upon the active surface of a corresponding cam having a helicoidal profile made on the lateral surface of said cylindrical hole, with manual activating means being adapted and arranged for controlling the rotation of said small piston around its own axis, and hence, the axial shifting of said small piston itself, in the spring compressing sense, for converting said demand valve from said second configuration into said first configuration.

2. A commutator device according to claim 1, characterized in that said activating means comprise a rotatable sleeve, coaxial with said small piston and interposed between the latter and said cylindrical hole, said sleeve being provided with axial slits inside each of which there is inserted one of said stakes, and with an actuating handle that protrudes above said cover.

3. A commutator device according to claim 1 or 2, characterized in that said sleeve is provided with a bottom base wall adapted for constituting a support for said spring, and with a projection protruding axially from said base wall, adapted to be inserted into said spring for axially centering it.

4. A commutator device according to claim 1 or 2, characterized in that said cover comprises an annular relief, coaxial with said hole, disposed around it and provided with an annular rim protruding radially from said annular relief, said actuating handle of said element being provided with a first flat wall adapted for resting upon said annular relief and on said annular rim, and with a second cylindrical wall, peripherally outside said annular rim adapted for being disposed around it, at least a part of said second cylindrical wall being provided with elastic fixing means adapted for being inserted springwise on said cover, for axially blocking said actuating handle with respect to the cover itself.

5. A commutator device according to claim 4, characterized in that said elastic fixing means comprise radial cuts made on said first and second walls of the actuating handle, which are adapted for rendering elastically deformable the sector of said handle which is comprised between two contiguous cuts, and through radial teeth made on the inner surface of said second wall that are adapted for being coupled with said annular rim.

6. A commutator device according to claim 4, characterized in that there are also provided stopping means which are adapted for delimiting the rotation of said handle with respect to said annular rim between two predetermined angular positions that are out of phase at an angle which is necessary for rotating said activating handle for taking said small piston from the axial position in which it is disposed in said second configuration into the axial position in which it is disposed in said first configuration.

7. A commutator device according to claim 6, characterized in that said stopping means comprise a radial protuberance, made on said annular relief of the cover, adapted for cooperating with said radial teeth of said second handle wall.

8. A distributor device according to claim 4, characterized in that on said first handle wall at least one aperture is provided that is adapted for uncovering parts of the surface of said annular relief and said annular rim for furnishing a visual indication of said prefixed angular positions.

9. A device according to claim 8, characterized in that said cover comprises an annular relief adapted for being aligned with said aperture following the rotation of said handle for furnishing a tactile indication of said predetermined angular positions.

* * * * *